United States Patent [19]

Potter

[11] 4,243,567

[45] Jan. 6, 1981

[54] MEDICAL COMPOSITIONS

[75] Inventor: William D. Potter, Bishop's Stortford, England

[73] Assignee: Smith & Nephew Research Limited, Harlow, England

[21] Appl. No.: 856,938

[22] Filed: Dec. 2, 1977

[30] Foreign Application Priority Data

Dec. 3, 1976 [GB] United Kingdom ............... 50578/76
Jun. 3, 1977 [GB] United Kingdom ............... 23789/77
Nov. 18, 1977 [GB] United Kingdom ............... 48193/77

[51] Int. Cl.³ ............................................. C08L 33/02
[52] U.S. Cl. ................. 260/29.6 MM; 260/29.6 MP; 260/29.6 AT; 260/42.18; 260/42.29
[58] Field of Search ........ 260/42.18, 42.29, 29.6 MM, 260/29.6 MP, 29.6 AT; 128/90

[56] References Cited

U.S. PATENT DOCUMENTS 4,044,761 8/1977 Hall .................................... 260/42.29
4,102,338 7/1978 Parker .................................... 128/90

FOREIGN PATENT DOCUMENTS 2621003 12/1976 Fed. Rep. of Germany ............. 128/90
1316129 5/1973 United Kingdom .

Primary Examiner—Lewis T. Jacobs
Attorney, Agent, or Firm—Sprung, Felfe, Horn, Lynch & Kramer

[57] ABSTRACT

Cements for medical or industrial purposes contain watersoluble borate or phosphate glasses including multivalent ions e.g. zinc, aluminium or calcium and a poly (carboxylic acid) such as polyacrylic acid. As the glass dissolves ions or other reactive species crosslink the polymer.

28 Claims, No Drawings

MEDICAL COMPOSITIONS

This invention is concerned with improvements in and relating to curable compositions of the so-called "polycarboxylate cement" type and to the preparation thereof. Whilst it is especially directed to the production of splinting bandages loaded with such compositions, it has general utility in the field of cements for medical and nonmedical e.g. constructional uses.

Compositions for the production of polycarboxylate cements, as described for example in British Pat. No. 1,316,129, generally comprise two principal components, namely a poly (carboxylic acid) or precursor therefor, and an ion-leachable glass, generally in powdered form. When the two components are brought into contact in the presence of water, ions are leached out from the glass and lead to the cross-linking of the polymer to form a polycarboxylate cement.

It has now been found, in accordance with the present invention, that the ions used to cross link the poly (carboxylic acid) may be provided by certain glasses containing at least one multivalent metal (i.e. a metal of valency two or more) which glasses are wholly or substantially soluble in the presence of water and such polycarboxylic acid to form at least one reactive component capable of cross linking a poly (carboxylic acid). Glasses of this type, which can be used in the process and compositions of the present invention are described in British patent application Nos. 23789/77 and 48193/77.

The use of compositions containing such water-soluble glasses offers a number of advantages as compared to the use of compositions containing ion-leachable glasses.

The most likely predominant mechanism appears to be that the small particles of glass are progressively dissolved or eroded to give metal ions in solution which link with the —COOH groups of suitably adjacent polymer chains to cause crosslinking. It is however conceivable that pH conditions are such that the metal re-precipitates as oxide or hydroxide once dissolved; in such a case the —COOH groups could link to a common precipitated particle to give a cross-linking effect. Also, it is possible that (especially as the original glass particles grow smaller) they themselves become similarly chemically bound and immobilised to various polymer chains, giving a different form of cross-linking. It is intended in the present invention to cover all these possibilities.

In normal conditions it is expected that substantially all the multivalent metal ions in a water-soluble glass will be released on dissolution of the glass. With an ion-leachable glass as in the prior art only a proportion of such ions are released, and this proportion is not easily quantifiable. Accordingly it is now possible to calculate more accurately the amount of multivalent ions available for cross-linking the poly (carboxylic acid) in the case of the water-soluble glasses than in the case of ion-leachable glasses. In the latter case the rate and amount of multivalent ion release will depend upon various factors such as, for example, the composition of the glass, the concentration of carboxylic groups in the polymer and the state of subdivision of the glass. The present system provides release of ions which is irrespective of the amount of polymer at least until there are substantial changes of pH i.e. towards the end of the reaction, and therefore the setting reaction does not slow down until towards the very end of the process. Further, since the amount of multivalent ion release is independent of the carboxylic acid group content of the polymer it is possible using a water-soluble glass to cross-link polymers having a lower concentration of carboxylic acid groups than would be attainable using the ion-leachable glasses of the prior art.

There is also the possibility of using a poly (carboxylic acid) which is already partly cross-linked and water-soluble; such a gelled material would not be mobile enough for use with the static ion-leachable glass particles.

Accordingly, one aspect of the invention provides a method for the production of a cement which comprises bringing into contact (a) a phosphate or borate glass containing at least one multivalent metal, said glass being present in particulate and/or fibrous form and being wholly or substantially soluble in aqueous conditions to form at least one reactive component capable of cross-linking a poly (carboxylic acid) and (b) a poly (carboxylic acid) or precursor therefor or partially cross-linked form thereof and (c) an aqueous medium, preferably water.

The man skilled in the art will realise that the particles or fibres can be free-flowing and separate or can possibly be part of a structure e.g. a woven or non-woven fabric or a foam or other matrix.

The glasses used in accordance with the invention must be water-soluble preferably completely but in all cases substantially or almost completely. They should be soluble moreover at common ambient temperatures (e.g. 5°-30° C.). While the applicants do not wish to be bound to this feature in the broad scope of their invention, they have found for most of the glasses utilised the composition and particle size in such that the glass dissolved, with constant agitation in excess water within 10 minutes to one hour, e.g. in about 20 minutes, at ambient temperatures.

It is conceivable that a small proportion of each glass particle will remain undissolved in practice of the invention and provide a reinforcing filler medium in the eventual cement, as discussed above.

Secondly, the glasses must contain at least one multivalent metal, preferably calcium, aluminium or zinc, but possibly magnesium or barium and for non-medical uses possibly also iron, chromium, copper or vanadium. It appears that such metals are generally present in such a form that on dissolution in water the metals are released in ionic form.

It is preferred for some purposes for the glasses according to the invention to be based on borate (measured as boric acid, $B_2O_3$) since these give a cement which is water resistant after setting. Glasses based on phosphates ($P_2O_5$ glass) give a water-softenable cement with a different range of uses.

The multivalent metal, again measured in the glass as its oxide provides for cross-linking as the glass dissolves and also modifies the rate of dissolution of the glass. It is possible in either the borate or phosphate glass to use only a two-component glass e.g. $B_2O_3/ZnO$ or $P_2O_5/ZnO$ but it is preferred in each case to add a further oxide, preferably $Al_2O_3$ but possibly CaO, in small amounts to reduce the rate of dissolution and thus alter the handling properties of the cement while wet.

Up to 2% of silica and small amounts (up to 5%) of sodium can also be present in the glass to modify its rate of dissolution. Too much monovalent ion, however, affects the degree of cross-linking.

In some applications part of the zinc oxide may be replaced by up to 10 mole percent of magnesium oxide, the magnesium also providing a cross-linking inducing cation for a PAA cement. Suitable compositions for such glasses, which may have a zero alumina content are as follows, all percentages being mole percent.

| Boric Oxide | Zinc Oxide | Magnesium Oxide |
|---|---|---|
| 38.4 | 59.5 | 1.9 |
| 38.6 | 55.7 | 5.7 |
| 38.6 | 51.9 | 9.5 |

In all these compositions the alumina and/or the magnesium oxide content determines the water solubility of the material. Increasing the content of one or both oxides decreases the water solubility.

In further applications small quantities of other solubility determining oxides may be added to the composition. Thus, alkaline earth oxides and silica decrease the water solubility whereas alkali metal oxides increase the solubility.

Such glasses will generally be prepared by fusing together the glass-forming components (e.g. on the one hand boric acid in the case of borate glasses or polyphosphoric acid or an alkali metal polyphosphate in the case of the phosphate glasses, and on the other hand the multivalent metal oxide or a precursor therefor) at an appropriate temperature usually 800°–1400° C., and causing or allowing the final mixture to cool to form a glass. Such glasses are in fact easy to melt and prepare in particulate form.

Broadly speaking from 10 to 65 mole percent multivalent metal oxide will be present in the glass, and not more than 15 mole percent of further oxide to modify rate of dissolution, but the amount will vary depending upon the nature of the composition in which the glass is to be used.

A preferred specific composition is form 35–50 mole percent of $B_2O_3$, 0–15 mole percent (preferably 0–5) of $Al_2O_3$ and 10–65 mole percent (preferably 35–65) of ZnO.

For example the total amount of cation to be released expressed in terms of grams of metal oxide per gram of poly (acrylic acid) in the cement is shown below:

| Cation | Gram of metal oxide per gram of poly (acrylic acid) |
|---|---|
| $Ca^{2+}$ | 0.38 |
| $Zn^{2+}$ | 0.565 |
| $Al^{3+}$ | 0.472 |

The cation content has been expressed in terms of the oxides since it appears important to neutralise the poly (acrylic acid) during the setting reaction. If a borate glass is used, it is unlikely that the borate union will interfere with tne neutralisation reaction, but the situation may be more complex in the case of a phosphate glass and additional metal oxide may be required.

The ratio by weight of glass to poly (carboxylic acid) should usually lie in the range between 3:1 and 1:1. Assuming complete dissolution of the glass, the metal oxide content for each cation is shown in the table below:

| Metal Oxide | Glass / Acid Ratio | |
|---|---|---|
| % in glass | 1/1 | 2/1 |
| CaO | 38% | 19% |
| ZnO | 56% | 28% |
| $Al_2O_3$ | 47% | 23% |

For convenience in handling and in order to ensure rapid dissolution the water-soluble glass will preferably be employed in finely divided particulate form, e.g. with a particle maximum dimension below 250 microns and preferably less than 75 or even 50 microns.

Generally spherical particles are preferred and theoretically a close ratio of sizes is valuable for uniformity. In practice we have used four classified grades of glass particles, 0–75, 0–38, 10–75 and 10–38 microns.

The poly (carboxylic acids) are usually based on unsaturated monocarboxylic acids, and their anhydrides and unsaturated dicarboxylic acids and their anhydrides being homopolymers of any one of these, copolymers between any two or more of these or copolymers between one or more of these and one or more further ethylenically unsaturated monomers. Specific compounds are acrylic, itaconic, mesaconic, citraconic, or maleic acid, or anhydrides thereof.

Preferred homopolymers are acrylic acid or acrylic acid anhydride homopolymers. Copolymers with acids preferably utilise acrylic acid with acrylamide or acrylonitrile as the ethylenically unsaturated comonomer, or maleic acid with vinyl methyl ether. Copolymers with anhydrides preferably use ethylene, propylene, butene, or styrene for this purpose as the ethylenically unsaturated comonomer, e.g. maleic anhydride/ethylene copolymer.

The number average molecular weight of the polymeric material may be from 1,000 to 1,000,000, values of 50,000 to 5000,000 being preferred.

However, as stated above, partially cross-linked gellable polymeric materials could also be used, such as the polyacrylic acid material partially cross-linked with diallyl sucrose known under the Registered Trade Mark of "CARBOPOL."

The invention also provides a curable composition comprising (a) a water-soluble glass as described above and (b) the poly (carboxylic acid) or precursor therefor or partially cross-linked form thereof, optionally together with an inert reinforcing filler.

The curable composition may be formulated in different ways. Thus in accordance with one embodiment the present invention envisages a two-part package of (a) particulate and/or fibrous glass and (b) the polymeric acid or partially cross-linked form thereof, preferably in the form of an aqueous solution. There is also the possibility of providing the acid or anhydride as dry powdered material separate from the particulate and/or fibrous glass, for mixing together and subsequent activation by adding water. Both of these possibilities find utility in the field of dental and surgical cements.

It may be desirable to incorporate a reinforcing filler in the composition (e.g. in association with the water-soluble glass) and suitable fillers include finely divided inorganic material which is not water-soluble such as silicate glasses, quartz, alumina, titania, zircon and the like. Fillers are of course cheaper than the specialised glass component. Preferred filler particle sizes range up to 250 microns overall (particles) or 250 microns maximum diameter and 3 mm length (fibres) and most preferably below 75 microns e.g. from 5 to 50 microns. A filler with a suitable particle size distribution for close packing is particularly valuable. A possible weight range of filler is from 5 to 50 percent by total weight. Organic fillers, such as sawdust or milled polyvinylchloride scrap, are possible if the resultant shrinkage levels are acceptable.

It is a major aspect of the invention to provide the curable composition as an intimate particulate mixture of the particulate and/or fibrous glass and particulate polymeric acid or anhydride, (or precursor therefor or partially cross-linked form thereof), optionally together with the particulate inert. The weight ratio (glass; polymer) is suitably from 0.5:1 to 5:1, preferably from 1:1 to 3:1. The polymer preferably has a particulate size below 150 microns.

It is also valuable if such a particulate mixture contains a minor proportion of a hydroxycarboxylic acid, specifically tartaric acid, to assist workability and increase eventual tensile strength. Up to 20% of such acid by weight, based on the weight of the poly (carboxylic acid) is envisaged, and from 5 to 15% is preferred.

Another additive which can be incorporated is sodium chloride as an antishrinkage agent. Surprisingly, we have found that the inherent linear shrinkage of cements made according to the invention is only about 2.5% maximum compared to a shrinkage of about 10% in prior art materials of the ionleachable glass type, even though all of these latter still possess a substantial volume of substantially unchanged glass particles after setting. Thus, a small addition of sodium chloride, under 5% by total weight, is adequate to overcome shrinkage problems in the present invention, which is advantageous since too much sodium tends to compete with cross-linking ions.

Such particulate mixtures can be presented for use as a two-part pack comprising (a) the mixture and (b) a suitable amount of water, but is most usefully presented in association with a substrate in the form of a flexible carrier which is porous or otherwise provided with interstices. The mixture may be located at the surface of the flexible carrier, or within the pores of interstices, or both.

A major aspect of the invention is constituted by a splinting bandage wherein an intimate particulate mixture of the glass as described above and the polymeric material as described above possibly together with the filler as described above is carried on and/or intermingled with the fibres of a fibrous bandage substrate.

The total coating weight of such a bandage can be from 200 to 500 g/m², i.e. of the order of ten times that of the bandage itself.

The fabric of such a bandage is preferably a Leno weave cotton gauze, as conventional in this art. However, other woven or non-woven (stitched or netted) substrates based on multifilamentary or spun yarns comprising synthetic polymers e.g. polyamides, polyolefins and especially polyesters are also envisaged.

Such bandages may be formed by contacting the substrate with a slurry containing the particulate and/or fibrous glass and the polymer in an anhydrous liquid and allowing this liquid to evaporate. Contacting can be effected by dipping, brushing, spraying or like manipulative steps but is preferably done by spreading. The solids content of the slurry can be greater than 50% by weight. The anhydrous liquid is preferably a volatile organic medium e.g. methylene chloride. Usually an adhesive or binder will be present in the anhydrous medium, being soluble both in the said medium and in water serving to minimise loss of solids when the eventual bandage is dipped into the water prior to use. Up to 5% e.g. from 2.5 to 5% of the binder is preferable, (based on solids content of slurry) and hydroxyalkyl cellulose, specifically hydroxypropyl cellulose are valuable for this purpose.

Such bandages are dipped in water applied while wet to the patient, smoothed and manipulated into the desired shape, and allowed to gel and set. Water uptake is usually about 50% of powder loading, although we have found that the system as described above tolerates operator variability in this regard. A method of treating a human patient, or an animal, utilising such a bandage in the above-specified manner constitutes an aspect of the invention, as does the hardened and set bandage.

The invention will be further described with reference to the following examples in tabular form, in which the various headings have the following meanings;

(a) "COMP" means "Glass compositions in mole percentages," which are as follows:

| | | | | |
|---|---|---|---|---|
| I | 31.01 $SiO_2$ | 26.58 CaO | 36.39 $Al_2O_3$ | 6.02 $F_2$ (prior art) |
| II | 38.4 $B_2O_3$ | 61.1 ZnO | 0.5 $Al_2O_3$ | |
| III | 38.6 $B_2O_3$ | 61.4 ZnO | 0 $Al_2O_3$ | |
| IV | 38.6 $B_2O_3$ | 61.4 ZnO | 0 $Al_2O_3$ | (different melt of same batch) |
| V | 36.6 $B_2O_3$ | 62.6 ZnO | 0.8 $Al_2O_2$ | |
| VI | 38.2 $B_2O_3$ | 60.6 ZnO | 1.2 $Al_2O_3$ | |
| VII | 47.6 $B_2O_3$ | 17.3 ZnO | 0.5 $Al_2O_3$ | 34.6 MgO |
| VIII | 45.5 $P_2O_5$ | 54.0 ZnO | 0.5 $Al_2O_3$ | |
| IX | 46.0 $P_2O_5$ | 54.0 ZnO | | | n.b. All the above are batch ratios, before melting. There is negligible oxide loss except for $P_2O_5$, which loses a few percent (less than 10).

(b) "SIZE" shows minimum and maximum particle dimension in microns.

(c) "WEIGHT RATIOS" denote:
A—glass/polymer
B—tartaric acid/polymer
C—filler/polymer
D—NaCl/polymer
E—water/polymer (d) "RESULTS" are given as:
(i) "gel time"—in seconds
(ii) "set time"—in minutes and seconds
(iii) T="Tensile strength" in pounds/sq. in. (1 p.s.i. =70.4 gm/sq. cm.)
(iv) S="Shrinkage" measured as percentage linear shrinkage.

| | GLASS TYPE | | WT. RATIOS TO PAA | | | | | RESULTS | | | |
|---|---|---|---|---|---|---|---|---|---|---|---|
| EXAMPLE | COMP. | SIZE | A | B | C | D | E | GEL | SET | T | S |
| 1 | I | 0–75 | 3 | 0.1 | 0 | 0 | 0.5 | 110 | 11.25 | — | — |
| 2 | II | 10–75 | 3 | 0 | 0 | 0 | 0.5 | 29 | 5.72 | — | — |
| 3 | II | 10–75 | 3 | 0.1 | 0 | 0 | 0.5 | 25 | 7.0 | — | — |
| 4 | II | 5–75 | 3 | 0 | 0 | 0 | 0.5 | 38 | 7 57 | — | — |
| 5 | II | 5–75 | 3 | 0.1 | 0 | 0 | 0.5 | 38 | 7.42 | — | — |

-continued

| EXAMPLE | GLASS TYPE COMP. | SIZE | WT. RATIOS TO PAA A | B | C | D | E | RESULTS GEL | SET | T | S |
|---|---|---|---|---|---|---|---|---|---|---|---|
| 6 | II | 2-75 | 3 | 0 | 0 | 0 | 0.5 | 36 | 7.29 | — | — |
| 7 | II | 2-75 | 3 | 0.1 | 0 | 0 | 0.5 | 39 | 6.58 | — | — |
| 8 | II | 0-75 | 2 | 0 | 1 | 0 | 0.5 | 43 | 19.48 | — | — |
| 9 | II | 0-75 | 2 | 0 | 0.5 | 0 | 0.5 | 34 | 10.54 | — | — |
| 10 | II | 0-75 | 2 | 0 | 0 | 0 | 0.5 | 36 | 7.6 | — | — |
| 11 | II | 0-75 | 3 | 0 | 0 | 0 | 0.5 | 26 | 4.30 | — | — |
| 12 | II | 0-75 | 1 | 0 | 1 | 0 | 0.5 | 50 | 30+ | — | — |
| 13 | II | 0-38 | 1 | 0.1 | 0 | 0 | 0.5 | 15 | 30+ | — | — |
| 14 | II | 0-38 | 2 | 0.1 | 0 | 0 | 0.5 | 20 | 7.6 | — | — |
| 15 | II | 0-38 | 3 | 0.1 | 0 | 0 | 0.5 | 15 | 4 | — | — |
| 16 | II | 0-75 | 1 | 0.1 | 0 | 0 | 0.5 | 17 | 30+ | — | — |
| 17 | II | 0-75 | 2 | 0.1 | 0 | 0 | 0.5 | 30 | 12.24 | — | — |
| 18 | II | 0-75 | 3 | 0.1 | 0 | 0 | 0.5 | 34 | 7.42 | — | — |
| 19 | III | 0-75 | 3 | 0.1 | 0 | 0 | 0.5 | 30 | 2.45 | — | — |
| 20 | III | 0-75 | 2 | 0.1 | 0 | 0 | 0.5 | 43 | 9.42 | 795 | 2.4 |
| 21 | III | 0-75 | 2 | 0.1 | 0 | 0 | 0.5 | 42 | 6.54 | 712 | 2.4 |
| 22 | III | 0-75 | 2 | 0.1 | 0 | .15 | 0.5 | 34 | 3.42 | 725 | 0.86 |
| 23 | III | 0-75 | 2 | 0.1 | .15 | .15 | 0.5 | 35 | 4.12 | 660 | 0.84 |
| 24 | III | 0-75 | 2 | 0.1 | .3 | .15 | 0.5 | 37 | 4.56 | 628 | 0.56 |
| 25 | IV | 0-38 | 3 | 0.1 | 0 | 0 | 0.5 | 35 | 4.15 | — | — |
| 26 | IV | 0-38 | 3 | 0.1 | 1 | 0 | 0.5 | 47 | 12.12 | — | — |
| 27 | V | 0-38 | 1 | 0.1 | 0 | 0 | 0.5 | 17 | 16.24 | — | — |
| 28 | V | 0-38 | 2 | 0.1 | 0 | 0 | 0.5 | 17 | 7.18 | — | — |
| 29 | V | 0-38 | 3 | 0.1 | 0 | 0 | 0.5 | 17 | 5.36 | — | — |
| 30 | V | 0-75 | 1 | 0.1 | 0 | 0 | 0.5 | 23 | 18.42 | — | — |
| 31 | V | 0-75 | 2 | 0.1 | 0 | 0 | 0.5 | 21 | 9.42 | — | — |
| 32 | V | 0-75 | 3 | 0.1 | 0 | 0 | 0.5 | 19 | 6.6 | — | — |
| 33 | VI | 0-38 | 1 | 0.1 | 0 | 0 | 0.5 | 15 | 16.42 | — | — |
| 34 | VI | 0-38 | 2 | 0.1 | 0 | 0 | 0.5 | 12 | 5.24 | — | — |
| 35 | VI | 0-38 | 3 | 0.1 | 0 | 0 | 0.5 | 15 | 3.12 | — | — |
| 36 | VI | 0-75 | 1 | 0.1 | 0 | 0 | 0.5 | 28 | 24 | — | — |
| 37 | VI | 0-75 | 2 | 0.1 | 0 | 0 | 0.5 | 20 | 9 | — | — |
| 38 | VI | 0-75 | 3 | 0.1 | 0 | 0 | 0.5 | 25 | 8.24 | — | — |
| 39 | VII | 0-75 | 2 | 0 | 0 | 0 | 1.0 | 60 | 30+ | — | — |
| 40 | VII | 0-75 | 3 | 0 | 0 | 0 | 1.0 | 45 | 30 | — | — |
| 41 | VIII | 0-75 | 1 | 0 | 0 | 0 | HIGH | 600 | 30 | — | — |
| 42 | IX | 0-75 | 1 | 0 | 0 | 0 | HIGH | 1200 | 60 | — | — |

The following operating Examples A and B also further describe the invention.

EXAMPLE A

A glass was prepared by co-melting for 30 minutes with stirring (ZnO), magnesium oxide (MgO), boric oxide ($B_2O_3$) and aluminium oxide ($Al_2O_3$) in the following molar proportions:

ZnO—17.3
MgO—34.6
$B_2O_3$—47.6
$Al_2O_3$—0.5

The glass was cooled by quenching on a steel table, powdered and samples were mixed with PAA followed by the addition of water. It was found that the mix rapidly evolved heat indicating an exothermic polymerisation reaction. This was rapidly followed by conversion to a smooth very thick paste after which solidification to the cement took place. The results are summarized in the following Table.

TABLE

| | Weight ratio-glass : PAA | |
|---|---|---|
| | 2:1 | 3:1 |
| Mix hot | 30 secs | 20 secs |
| Smooth thick paste | 1 min | 45 secs |
| Hard elastic solid | 50 mins | 30 mins |
| Complete setting | 24 hrs | 24 hrs |

The completely set cements were found to be stable and unaffected by immersion for 8 hours in boiling water

EXAMPLE B

Two phosphorus based glasses were prepared by co-melting zinc oxide, phosphorus pentoxide and aluminium oxide in the following molar proportions:

| Glass A | | Glass B | |
|---|---|---|---|
| ZnO | 54.0 | ZnO | 53.8 |
| $P_2O_5$ | 45.5 | $P_2O_5$ | 46.0 |
| $Al_2O_3$ | 0.4 | $Al_2O_3$ | 0.0 |

Cements were prepared from the glasses and PAA in a 1:1 weight ratio and the results are summarized in Table 2. The polymerisation inhibiting effect of the phosphoric acid slows down the initial reaction so that the initial release of heat is not so pronounced as with the borate glasses.

TABLE 2

| Glass | A | B |
|---|---|---|
| Mix tacky | 10 mins | 20 mins |
| Elastic solid | 30 mins | 1 hr |
| Hard solid | 1 hr | 16 hrs |

The cements so produced can be softened by soaking in water.

In some applications the same metal oxide may be employed both as the metal cation and as the glass modifying oxide.

I claim:
1. A method for the production of a cement which comprises bringing into contact (a) a phosphate or bo- rate glass containing at least one multivalent metal, said glass being present in particulate and/or fibrous form and being wholly or substantially soluble in aqueous conditions to form at least one reactive component capable of crosslinking a poly (carboxylic acid) and (b) a poly (carboxylic acid) or precursor therefor or partially crosslinked form thereof and (c) an aqueous medium.

2. A method as claimed in claim 1 in which the multivalent metal is zinc, aluminium, calcium, magnesium, barium, iron, chromium, copper or vanadium.

3. A method as claimed in claim 2 in which the glass is a two-component $B_2O_3$—ZnO glass.

4. A method as claimed in claim 2 in which the glass is a three-component $B_2O_3$—ZnO—$Al_2O_3$ glass.

5. A method as claimed in claim 3 in which the glass contains 35–50 mole percent of $B_2O_3$, 0–15 mole percent of $Al_2O_3$ and 10–65 mole percent of ZnO.

6. A method as claimed in claim 5 in which the glass contains, 35–50 mole percent of $B_2O_3$, 0–5 mole percent of $Al_2O_3$ and 35–65 mole percent of ZnO.

7. A method as claimed in claim 2 in which the glass is a two-component $P_2O_5$—ZnO glass.

8. A method as claimed in claim 2 in which the glass is a three-component $P_2O_5$—ZnO—$Al_2O_3$ glass.

9. A method as claimed in claim 1 in which the glass is in the form of generally spherical particles all of a maximum dimension less than 250 microns.

10. A method as claimed in claim 9 in which the said maximum dimension is 75 microns.

11. A method as claimed in claim 1 in which the poly (carboxylic acid) or its precursor is chosen from unsaturated monocarboxylic acids and their anhydrides, and unsaturated dicarboxylic acids and their anhydrides, being homopolymers of any one of these, copolymers between any two or more of these or copolymers between one or more of these and one or more further ethylenically unsaturated monomers.

12. A method as claimed in claim 11 in which the poly (carboxylic acid) or its precursor is a polymer of acrylic acid or acrylic acid anhydride.

13. A method as claimed in claim 11 in which the number average molecular weight of the said poly (carboxylic acid) or its precursor is from 1000 to 1000000.

14. A method as claimed in claim 1 in which the partially crosslinked form of the poly (carboxylic acid) is partially crosslinked with diallyl sucrose.

15. A curable composition comprising (a) a phosphate or borate glass containing at least one multivalent metal, said glass being present in particulate and/or fibrous form and being wholly or substantially soluble in aqueous conditions to form at least one reactive component capable of crosslinking a poly (carboxylic acid) together with (b) a poly (carboxylic acid) or precursor therefor or partially crosslinked form thereof.

16. A curable composition as claimed in claim 15 in which the glass component is one comprising a multivalent metal of zinc, aluminum, calcium, magnesium, barium, iron, chromium, copper or vanadium.

17. A curable composition as claimed in claim 15 in which the poly (carboxylic acid) or precursor or partially cross-linked form thereof is chosen from unsaturated monocarboxylic acids and their anhydrides, and unsaturated dicarboxylic acids and their anhydrides, being homopolymers of any one of these, copolymers between any two or more of these or copolymers between one or more of these and one or more further ethylenically unsaturated monomers.

18. A curable composition as claimed in claim 16 further including from 5 to 50 percent by total weight of a water-insoluble finely divided particulate inorganic filler of particle size below 250 microns.

19. A curable composition as claimed in claim 15 further including from 5 to 50 percent by total weight of a water insoluble fibrous inorganic filler of fibre diameter below 250 microns and fibre length below 3 mm.

20. A curable composition as claimed in claim 15, comprising an intimate particulate mixture of particles of glass (a) and particles of polymer (b).

21. A curable composition as claimed in claim 20 further including from 5 to 50 percent by total weight of a water-insoluble finely divided particulate inorganic filler of particle size below 250 microns.

22. A curable composition as claimed in claim 20 further including from 5 to 50 percent by total weight of a water-insoluble fibrous inorganic filler of fibre diameter below 250 microns and fibre length below 3 mm.

23. A curable composition as claimed in claim 20, in which the weight ratio between the glass (a) and polymer (b) is from 1:1 to 3:1.

24. A curable composition as claimed in claim 20 in which the particles of polymer (b) are of less than 150 microns particle size.

25. A curable composition as claimed in claim 20 which contains mixed therewith up to 20% by weight based on polymer (b) of a particulate hydroxycarboxylic acid.

26. A curable composition as claimed in claim 25 in which the hydroxycarboxylic acid is tartaric acid present in an amount of 5 to 15% by weight of polymer (b).

27. A curable composition as claimed in claim 20 further containing up to 5% by weight of dry particulate sodium chloride mixed therewith.

28. A curable composition as claimed in claim 20 associated with a substrate in the form of a flexible carrier which is porous or otherwise provided with interstices.

* * * * *